United States Patent
Inoue

(10) Patent No.: US 6,970,739 B1
(45) Date of Patent: Nov. 29, 2005

(54) IONTOPHORESIS DEVICE

(75) Inventor: Kazutaka Inoue, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 0 days.

(21) Appl. No.: 10/111,616

(22) PCT Filed: Oct. 26, 2000

(86) PCT No.: PCT/JP00/07493

§ 371 (c)(1),
(2), (4) Date: Apr. 26, 2002

(87) PCT Pub. No.: WO01/30441

PCT Pub. Date: May 3, 2001

(30) Foreign Application Priority Data

Oct. 28, 1999 (JP) ................................. 11-306392

(51) Int. Cl.[7] ................................................ A61N 1/30

(52) U.S. Cl. ....................................................... 604/20

(58) Field of Search .......................................... 604/20

(56) References Cited

U.S. PATENT DOCUMENTS

| | | | | |
|---|---|---|---|---|
| 5,306,235 A | * | 4/1994 | Haynes | 604/20 |
| 5,697,896 A | * | 12/1997 | McNichols et al. | 604/20 |
| 6,047,208 A | * | 4/2000 | Flower | 604/20 |
| 6,141,582 A | * | 10/2000 | Mori et al. | 604/20 |
| 6,148,232 A | * | 11/2000 | Avrahami | 604/20 |
| 6,295,469 B1 | * | 9/2001 | Linkwitz et al. | 604/20 |
| 6,505,079 B1 | * | 1/2003 | Foster et al. | 607/68 |

* cited by examiner

Primary Examiner—Michael J. Hayes
(74) Attorney, Agent, or Firm—Townsend & Banta

(57) ABSTRACT

This is an iontophoresis device preferred to detect abnormal conductivity at the beginning of energization and during energization. The iontophoresis device has a device (50) as a power source and the device (50) comprises an electric energy generating portion (60) generating electric energy, an output portion (70) outputting the electric energy, and an abnormal conductivity detecting portion (80) detecting whether or not the electric energy is supplied normally. The detecting action of the abnormal conductivity detecting portion (80) is carried out at the time of the non-output action of the output portion (70). During the energization, the output action by the output portion (70) and the detecting action by the abnormal conductivity detecting portion (80) are alternated in response to a command received from the microcomputer (12).

10 Claims, 2 Drawing Sheets

IONTOPHORESIS DEVICE

TECHNICAL FIELD

The present invention relates to an iontophoresis device applied to transdermal or transmucosal administration, more particularly, having a function for detecting abnormal conductivity.

BACKGROUND ART

The iontophoresis is a system used for quickening skin absorption with electricity. The object of the iontophoresis is to quicken permeation of medicine molecules through the skin barrier with good use of a force that moves positively charged molecules from positive pole to negative pole and negatively charged molecules from negative pole to positive pole in an electric field generated mainly due to current conducting. [Refer to (Journal of Controlled Release) pp. 213 to 220, Vol. 18, 1992; Advanced Drug Delivery Review) p. 119, Vol. 9, 1992; Pharmaceutical Research) pp. 318 to 326, Vol. 3, 1986.]

Such an iontophoresis device having been known well is provided with means for checking whether or not the movement of molecules (including drugs) is done normally. The checking means in this case may be, for example, a method for measuring an output current with respect to a voltage output from an applied DC. According to this method, a conducting or non-conducting state is checked by applying a comparatively high voltage to the object spot at the beginning of energization. When the output current is in a predetermined value or less, it is decided as abnormal, thereby the voltage output stops.

The official gazette of National Publication of International Patent Application No. 10-510179 discloses a power-driven transportation unit used to monitor both current and voltage of the power-driven transportation. This transportation unit, when the impedance on the object human skin is stabilized for a predetermined time after the device is started up, begins monitoring of both current and voltage of the transportation. When the monitored value is not within a predetermined value, the output stops.

In case of the above described method that makes the monitoring by applying a comparatively high voltage to the object spot at the beginning of energization, however, a problem arises; concretely, the high output voltage makes the user feel malaise. In addition, the above described method which begins monitoring of both current and voltage of the power-driven transportation after the impedance on the object spot skin is stabilized is to be confronted with another problem that the current conducting state cannot be confirmed until the impedance on the object spot skin is stabilized.

Under such circumstances, it is an object of the present invention to solve the above conventional problems and provide an iontophoresis device preferred to detect abnormal conductivity at the beginning of energization and during energization.

DISCLOSURE OF THE INVENTION

The inventors have examined the conventional techniques to solve the above described problems. And, as a result, the present invention has been achieved by finding the fact that an abnormal conductivity detecting means is provided for detecting whether or not supply of electric energy is normal, and then abnormal conductivity can be effectively detected at the beginning of energization and during energization, by performing the detecting action of the abnormal conductivity detecting means that is carried out at the time of the non-output action of the device. In other words, according to the present invention, at the beginning of energization, the abnormal conductivity detecting means detects whether or not the supply of electric energy is normal with reference to a preset high impedance. When the result is determined as normal, the device starts an output action of the electric energy at a low impedance preset for medication. When the result is determined as abnormal, the device does not start the output action of the electric energy. On the other hand, during energization, the output action by the electric energy and the detecting action by the abnormal conductivity detecting means are alternated, so that the output action of the electric energy stops when the supply of electric energy is determined as abnormal by the abnormal conductivity detecting means.

An iontophoresis device according to the present invention comprises a preparation having a pair of electrodes and a device for supplying electric energy to the preparation, wherein the device includes an electric energy generating portion generating electric energy, an output portion outputting the electric energy to the preparation, and an abnormal conductivity detecting portion detecting whether or not the electric energy is supplied normally, wherein the detecting action of the abnormal conductivity detecting portion is carried out at the time of the non-output action of the output portion.

In this case, it is desirable that the output action by the output portion and the detecting action by the abnormal conductivity detecting portion are alternated. It is also desirable that the device has an alarm outputting an alarm sound when the abnormal conductivity detecting portion decides the supply of electric energy as abnormal, as well as that the output action by the output portion stops when the abnormal conductivity detecting portion decides that the abnormal supply of the electric energy is continued for a certain time.

A device for iontophoresis according to the present invention comprises an electric energy generating portion generating electric energy, an output portion outputting the electric energy, and an abnormal conductivity detecting portion detecting whether or not the electric energy is supplied normally, wherein the detecting action of the abnormal conductivity detecting portion is carried out at the time of the non-output action of the output portion. In this case, it is desirable that the output action by the output portion and the detecting action by the abnormal conductivity detecting portion are alternated. The abnormal conductivity detecting portion is provided with an amplifier circuit as needed and a diode is provided at the output terminal of the output portion as needed.

BEST MODE FOR CARRYING OUT THE INVENTION

Figure 1:
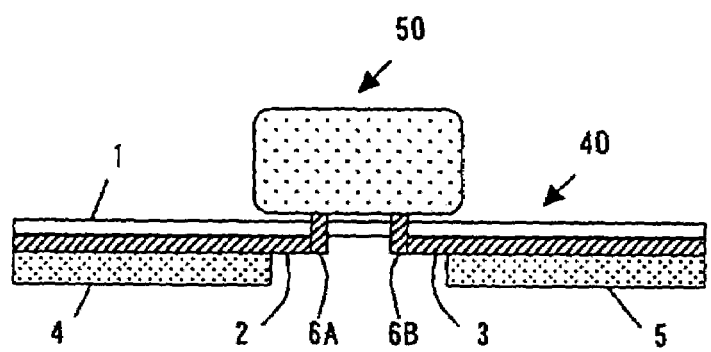
FIG. 1 is a conceptual cross-sectional view of an iontophoresis device of the present invention.

FIG. 1 is a conceptual cross-sectional view of the iontophoresis device of the present invention. This device, as shown in FIG. 1, comprises a preparation 40 for iontophoresis holding a medicine and a device 50 for iontophoresis that functions as a power source that generates electric energy required for this preparation to supply the medicine to the object skin or mucosa.

The iontophoresis preparation 40 is composed of an insulating substrate 1, a pair of electrodes 2 and 3 disposed on the insulating substrate 1 with a space therebetween, a medicine pool 4 disposed in contact with the electrode 2, an electrolyte pool 5 disposed in contact with the electrode 3, and tabs 6A and 6B used to attach the device 50 to the preparation 40. The tabs 6A and 6B are connected to the electrodes 2 and 3 respectively. When the iontophoresis preparation is provided with two or more medicine pools, the electrolyte pool is replaced with one of the medicine pools. The medicine and electrolyte pools are stuck, for example, on an object skin or mucosa directly or indirectly.

Figure 2:
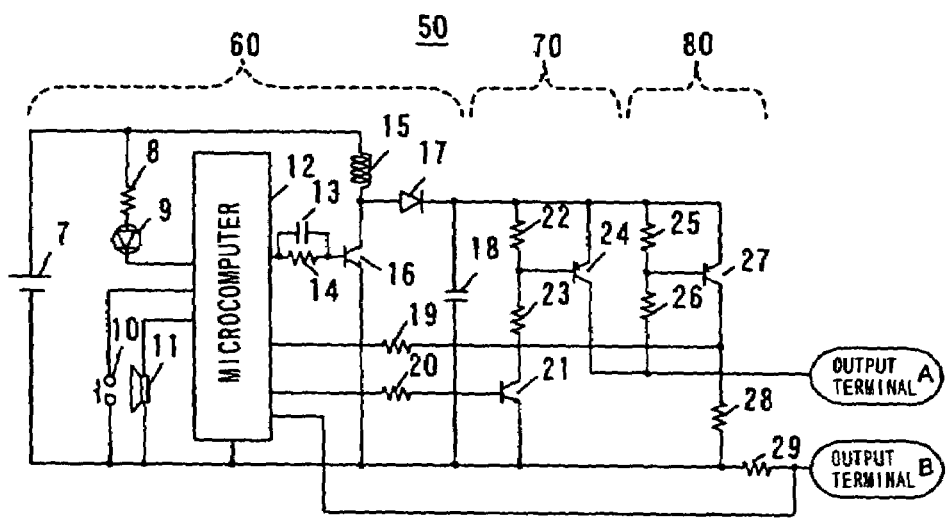
FIG. 2 is a circuit diagram of an iontophoresis device.

FIG. 2 is a circuit diagram of the device 50 for iontophoresis. As shown in FIG. 2, the device 50 is provided with an electric energy generating portion 60 that generates electric energy, an output portion 70 that outputs the electric energy to the output terminals A and B, and an abnormal conductivity detecting portion 80 that detects whether or not the electric energy is supplied normally.

The electric energy generating portion 60 is provided with a power source 7 composed of a battery, etc., a coil 15 connected to the power source 7, a transistor 16 and a diode 17 connected to the coil 15 respectively, an electric energy accumulating capacitor 18 connected to the diode 17, and a circuit in which a capacitor 13 and a resistor 14 are disposed in parallel so as to be connected to between the base of the transistor 16 and a microcomputer 12. In this case, the capacitor 13 is used to quicken the switching of the transistor 16 and the resistor 14 is used to limit the current that flows to the transistor 16.

Furthermore, as shown in FIG. 2, a circuit in which a resistor 8 and a light emission diode (LED) 9 are disposed serially is provided between the microcomputer 12 and the positive pole of the power source 7. In this case, the resistor 8 is used to limit the current that flows to the LED 9. A power switch 10 and an alarm buzzer 11 are connected to between the microcomputer 12 and the negative pole of the power source 7 as needed. The power switch 10 is used to start or stop the iontophoresis device.

The output portion 70 is provided with resistors 22 and 23 connected to both ends of the capacitor 18 serially, a transistor 21, and a transistor 24 having an emitter connected to one end of the resistor 22, a collector connected to an output terminal A, and a base connected to between the resistors 22 and 23, and a resistor 20 connected to between the base of the transistor 21 and the microcomputer 12. In this case, the resistor 20 is used to limit the current that flows to the transistor 21 and the resistor 22 is used to pull up the transistor 24. The resistor 23 is used to limit the base current of the transistor 24.

The abnormal conductivity detecting portion 80 is provided with resistors 25 and 26 connected serially to both ends of the transistor 24, a transistor 27 having an emitter connected to one end of the resistor 25, a collector connected to an output terminal B via resistors 28 and 29, and a base connected to between the resistors 25 and 26; and a resistor 19 connected to between the collector of the transistor 27 and the microcomputer 12. In this case, the resistor 19 is used to protect the input terminal of the microcomputer 12. And, as shown in FIG. 2, a junction between the resistor 29 and the output terminal B is connected to the microcomputer 12.

Next, the basic operation of the device 50 will be described with reference to FIG. 2.

At first, the output of the device 50 is transferred at a high impedance generated by the resistors 25 and 26, since the transistor 24 is in the non-conducting state before the device is operated for a patient. When the device is started for a patient, that is, when a load is connected to between the output terminals A and B, a weak current flows in the path denoted by reference numerals and characters 7-15-17-25-26-A-B-29-7 shown in FIG. 2. In the abnormal conductivity detecting portion 80, the resistor 25 lowers the base voltage of the transistor 27 due to this weak current. As a result, the transistor 27 goes into the conducting state. When the transistor 27 goes into this conducting state such way, a voltage almost equal to the battery voltage is generated at the upper end of the resistor 28 (at the connector side of the transistor 27). In this case, the electric energy supply is normal, thereby the microcomputer 12 is started up automatically. When the voltage at the upper end of the resistor 28 does not satisfy a predetermined value for any reason, however, the electric energy supply is abnormal. Therefore, the microcomputer 12 is not started up at this time. The detecting action of the abnormal conductivity detecting portion 80 is carried out at the time of the non-output action of the output portion 70.

When the electric energy supply is normal, the microcomputer 12 that starts up automatically turns on the LED 9, then sends a signal to the transistor 16 so that the transistor 16 oscillates in accordance with a pre-programmed pattern, thereby raising the voltage of the power source 7. According to the oscillation of the transistor 16, a counter electromotive force is generated in the coil 15 as needed. This counter electromotive force is accumulated as needed in the capacitor 18 via the diode 17, thereby the voltage of the power source 7 rises. The risen voltage accumulated in the capacitor 18 is sent to the output terminal A, since the transistor 21 goes into the conducting state in response to a signal received from the microcomputer 12, thereby the transistor 24 goes into the conducting state. When the transistor 24 goes into the conducting state, the transistor 27 goes into the non-conducting state.

Consequently, a current flows to the load connected to between the output terminals A and B, thereby a voltage is generated in the resistor 29 according to the current. Although it is difficult to detect this voltage at the beginning of energization, after a predetermined time passes the voltage is converted again to a current by an A/D converter located in the microcomputer 12, thereby it is measured. The microcomputer 12 changes the oscillation state of the transistor 16 according to this measured current, thereby the step-up voltage is adjusted to keep the output of the device 50 at a predetermined current. Such way, the output action of the output portion 70 is carried out.

After this, the device 50 switches the output action of the output portion 70 over to the detecting action of the abnormal conductivity detecting portion 80. The microcomputer 12 makes this switching and the transistors 21 and 24 go into the non-conducting state respectively. Consequently, a weak current flows again in the path denoted by the reference numerals and characters 7-15-17-25-26-A-B-29-7 or 18-25-26-A-B-29-18. As a result, the transistor 27 goes into the conducting state. If the detected voltage at the upper end of the resistor 28 is the predetermined value or more at this time, the conductivity becomes normal. The microcomputer 12 thus oscillates the transistor 16 in accordance with a pre-programmed pattern, thereby the abnormal conductivity detecting portion 80 is switched over to the output action of the output portion 70. Such way, when the conductivity is normal, the output action by the output portion 70 and the detecting action by the abnormal conductivity detecting portion 80 are alternated.

On the contrary, when the detected voltage at the top of the resistor 28 is lower than the predetermined value, the device 50 decides the conductivity as abnormal, thereby making the LED 9 blink and the buzzer 11 sound to issue an alarm. In the case where the conductivity is still abnormal a certain time after the alarm is issued, the device 50 stops the electric energy supply and makes the buzzer 11 sound and turns off the LED 9 to notify the operator of the stop of the output.

As described above, according to the present invention, the abnormal state at the application of the device is detected by alternating the output action by the output portion 70 and the detecting action by the abnormal conductivity detecting portion 80, thereby the safety of the user is assured.

In the above configuration of the device, the output is done in two ways; an output at a high impedance used to detect abnormal conductivity at the beginning of energization and an output at a low impedance used to dose a patient. The output values are preset.

The high impedance used for detecting abnormal conductivity is generated by the resistors 25 and 26 shown in FIG. 2. The impedance is affected and varied by such causes as the area of the object spot, the applied voltage, etc., so that the value is not limited specially; it can be set and varied according to circumstances. When the impedance is applied to a skin or mucosa, however, it must be set so as to be detected accurately with respect to the impedance of the skin or mucosa. The value should preferably be set within 100k ohms to 100M ohms. More preferably, the value should be set within 1M ohms to 10M ohms.

On the other hand, the low impedance used for dosing a patient is generated by the resistor 24 shown in FIG. 2, which is in the conducting state, as well as the resistor 29 provided as needed. Because the impedance is affected by the amount of an applied current, etc., the value is not limited. When the impedance is to be applied to a skin or mucosa, however, it should preferably be set within 1 ohm to 50k ohms to make the current sufficient. More preferably, the impedance should be set within 100 ohms to 5k ohms.

The period of the output action of the output portion 70 is not limited specially. However, it should preferably be set within one minute. More preferably, it should be set within one second. The period of the detecting action of the abnormal conductivity detecting portion 80 should preferably be set within several seconds. More preferably, it should be set within several $\mu$s to several ms. Because the switching is done quickly and efficiently, the conductivity state can be confirmed without affecting the output almost at all. The reason is as follows; the conductivity is kept due to a voltage left over in the load when the high impedance state ends quickly and a potential difference arises between the output voltage accumulated in the capacitor 18 and the voltage left over in the load due to a current generated at that time while the potential difference can be detected regardless of the output voltage by the abnormal conductivity detecting portion 80 provided between the output voltage accumulated in the capacitor 18 and the output terminal A.

Figure 3:
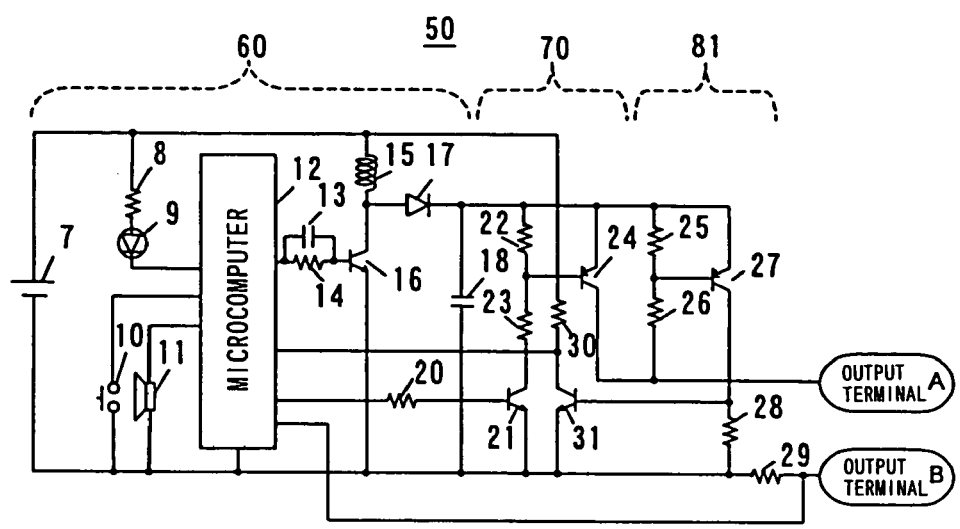
FIG. 3 is another circuit diagram of the iontophoresis device.
Figure 4:
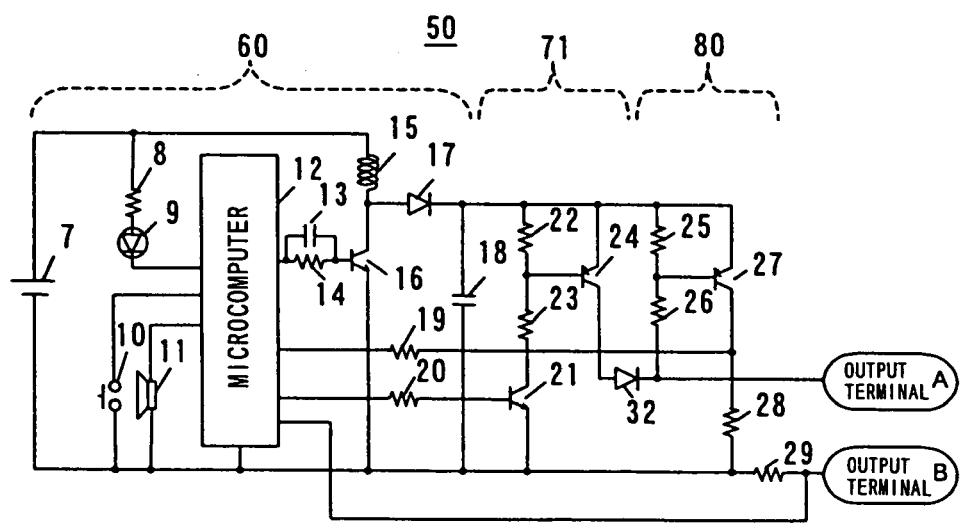
FIG. 4 is another circuit diagram of the iontophoresis device.

FIGS. 3 and 4 are other circuit diagrams of the device 50 for iontophoresis respectively.

The device 50 shown in FIG. 3 is provided with an amplifier circuit composed of a transistor 31 having a base connected to the upper end of the resistor 28 located in an abnormal conductivity detecting portion 81. This amplifier circuit drives the transistor 31 into the conducting state with a voltage lower than the voltage at the upper end of the resistor 28, which is recognized as being the predetermined value or less by the microcomputer 12 shown in FIG. 2. Consequently, a current flows into the resistor 30, so that the voltage at the lower end of the resistor 30 connected to the microcomputer 12 is sent to the microcomputer 12. The circuit in this example is especially effective when a satisfactory abnormal conductivity detecting accuracy is not obtained from the selection of a resistance value. In addition, in such a configuration of the device, because the upper end of the resistor 30 is connected to the battery voltage, the microcomputer 12 is protected from receiving of an excessive voltage, which is higher than the supply voltage.

There is another method for improving the abnormal conductivity detection accuracy. According to this method, a diode 32 is connected to the collector of the transistor 24 of the output portion 71 as shown in FIG. 4 to generate a potential difference between the voltage accumulated in the capacitor 18 and the voltage of the output terminal A, thereby increasing the value of the current flowing in the resistors 25 and 26. Every circuit in this case should preferably be configured so that the current consumption becomes within several $\mu$A to several tens of $\mu$A when the circuit operation stops.

As described above, because the iontophoresis device of the present invention enables alternation between the output action by the output portion and the detecting action by the abnormal conductivity detecting portion, removal of the device from the skin of the patient is decided as abnormal by the abnormal conductivity detecting portion, thereby the output from the output portion stops. In such a case, this device starts up automatically when it is stuck on the skin again, thereby the electric energy supply is continued.

When this device is provided with a slow start-up function, as well as other functions such as a total current amount adjusting function, etc., the safety of the device is more improved for such a case as where it is stuck again on the same living organism. In addition, when this device is further provided with constant current means that keeps a current (used to dose a patient) flowing at a low impedance at a predetermined value, the object human body is protected from excessive current flowing therein, thereby the safety of the device is more improved. It is also possible to warn the user to request an improvement when an abnormal impedance is detected. According to circumstances, the output stops to assure the safety.

The iontophoresis device of the present invention is employed desirably for local medication that limits the medication spots, especially for such spots as the neck, shoulders, waste, etc., where it is difficult to operate the power switch and to check such indicators as LEDs used to denote respective conductivity states. This device, when an abnormality is detected as a result of conductivity check performed at the beginning of energization and during energization, detects the abnormality, thereby the safety of the operator is assured. The device is such excellent in the usability.

INDUSTRIAL APPLICABILITY

According to the present invention, it is possible to obtain an iontophoresis device preferred to detect an abnormal conducting state at the beginning of energization and during energization.

What is claimed is:

1. An iontophoresis device comprising a preparation having a pair of electrodes and a device for supplying electric energy to the preparation, wherein the device includes:
    an electric energy generating portion generating electric energy for supplying a medicine,
    an output portion having an output action outputting the electric energy to the preparation and a non-output action outputting no electric energy for supplying a medicine, and
    an abnormal conductivity detecting portion taking a detecting action as to whether or not the electric energy is supplied normally,
    wherein the electric energy generating portion has circuitry-causing the abnormal conductivity detecting portion to take the detecting action at the time of the non-output action of the output portion, and an output action by the output portion and the detecting action by the abnormal conductivity detecting portion are alternated.

2. The iontophoresis device according to claim 1, wherein the device includes an alarm outputting an alarm sound when the abnormal conductivity detecting portion detects that supply of the electric energy as abnormal.

3. The iontophoresis device according to claim 2, wherein an output action by the output portion is stopped when the abnormal conductivity detecting portion detects that the abnormal state of the electric energy supply has continued for a predetermined time.

4. The iontophoresis device according to claim 1, wherein an output action by the output portion is stopped when the abnormal conductivity detecting portion detects that the abnormal state of the electric energy supply has continued for a predetermined time.

5. A device for iontophoresis comprising:
    an electric energy generating portion generating electric energy for supplying a medicine;
    an output portion having an output action outputting the electric energy to the preparation and a non-output action outputting no electric energy for supplying a medicine; and
    an abnormal conductivity detecting portion taking a detecting action as to whether or not the electric energy is supplied normally,
    wherein the electric energy generating portion has circuitry causing the abnormal conductivity detecting portion to take the detecting action at the time of the non-output action of the output portion, and an output action by the output portion and the detecting action by the abnormal conductivity detecting portion are alternated.

6. The device for iontophoresis according to claim 5, wherein the abnormal conductivity detecting portion has an amplifier circuit.

7. The device for iontophoresis according to claim 6, wherein the output portion has a diode disposed at its output end.

8. The device for iontophoresis according to claim 5, wherein the output portion has a diode disposed at its output end.

9. The device for iontophoresis according to claim 5, wherein the abnormal conductivity detecting portion has an amplifier circuit.

10. The device for iontophoresis according to claim 5, wherein the output portion has a diode disposed at its output end.

* * * * *